(12) United States Patent
Harashima et al.

(10) Patent No.: US 8,592,210 B2
(45) Date of Patent: Nov. 26, 2013

(54) POLYARGININE-MODIFIED LIPOSOME HAVING NUCLEAR ENTRY ABILITY

(75) Inventors: Hideyoshi Harashima, Hokkaido (JP); Shiroh Futaki, Kyoto (JP); Kentaro Kogure, Hokkaido (JP)

(73) Assignee: Japan Science and Technology Agency, Saitama (JP)

( * ) Notice: Subject to any disclaimer, the term of this patent is extended or adjusted under 35 U.S.C. 154(b) by 251 days.

(21) Appl. No.: 11/396,081

(22) Filed: Mar. 31, 2006

(65) Prior Publication Data
US 2007/0059353 A1    Mar. 15, 2007

Related U.S. Application Data

(63) Continuation of application No. PCT/JP2004/014500, filed on Oct. 1, 2004.

(30) Foreign Application Priority Data

Oct. 1, 2003   (JP) .................................. 2003-343857

(51) Int. Cl.
*A61K 48/00*   (2006.01)
*A61K 9/127*   (2006.01)
*C12N 15/88*   (2006.01)

(52) U.S. Cl.
USPC .......................................... 435/458; 424/450

(58) Field of Classification Search
USPC .......................................... 424/450; 435/458
See application file for complete search history.

(56) References Cited

U.S. PATENT DOCUMENTS

| | | | |
|---|---|---|---|
| 6,372,720 B1 * | 4/2002 | Longmuir et al. | 514/44 |
| 6,417,326 B1 | 7/2002 | Cullis et al. | |
| 6,482,826 B1 * | 11/2002 | Pierard | 514/254.07 |
| 2003/0072794 A1 * | 4/2003 | Boulikas | 424/450 |

FOREIGN PATENT DOCUMENTS

WO   WO-02/059147 A2   8/2002

OTHER PUBLICATIONS

Futaki, et al., Stearylated Arginine-Rich Peptides: A New Class of Transfection Systems, Bioconjugate Chem., 12 (6), 1005-1011, 2001.*
Kogure et al., Development of a non-viral multifunctional envelope-type nano device by a novel lipid film hydration method. J. Control Release. Aug. 11, 2004;98(2):317-23.*
Zhdanov et al Bioelectrochemistry. Nov. 2002;58(1):53-64. Cationic lipid-DNA complexes-lipoplexes-for gene transfer and therapy.*
H. Xinpu et al., "Synthesis of Surfactant Derived From Arginine and Modification to the Lipid Bilayer Membrane", Journal of Qiqihar Light Industry Institute, 6(4), 1990.*
Kogure, Kentaro et al., "Development of a non-viral multifunctional envelope-type nano device by a novel lipid film hydration method," *Journal of Controlled Release*, vol. 98:317-323 (2004).
Supplementary European Search Report for Application No. 04791967.5, dated Nov. 2, 2009.

* cited by examiner

*Primary Examiner* — Janet Epps-Smith
(74) *Attorney, Agent, or Firm* — Edwards Wildman Palmer LLP; Peter F. Corless; Christine C. O'Day

(57) ABSTRACT

With the object of providing a liposome having cellular and nuclear entry ability, to achieve this object, a liposome is provided having on its surface a peptide comprising multiple consecutive arginine residues, and specifically a liposome is provided wherein the peptide is modified with a hydrophobic group or hydrophobic compound and the hydrophobic group or hydrophobic compound is inserted into a lipid bilayer so that the peptide is exposed on the surface of the bilayer.

13 Claims, 7 Drawing Sheets

POLYARGININE-MODIFIED LIPOSOME HAVING NUCLEAR ENTRY ABILITY

CROSS-REFERENCE TO RELATED APPLICATIONS

This application is a continuation of PCT/JP2004/014500, filed on Oct. 1, 2004, which in turn claims priority from Japanese application no. JP 2003-343857, filed Oct. 1, 2003 the contents of which are incorporated herein by reference.

TECHNICAL FIELD

The present invention relates to a liposome having cellular and nuclear entry ability, and to a vector for cellular and nuclear delivery of target substances using the liposome.

BACKGROUND ART

In recent years many vectors and carriers have been developed for reliably delivering drugs, nucleic acids, peptides, proteins, sugar and the like to target sites. In the field of gene therapy, for example, retrovirus, adenovirus, adeno-associated virus and other virus vectors have been developed as vectors for introducing genes into target cells. However, because of such problems as difficulty of mass production, antigenicity, toxicity and the like associated with virus vectors, attention has shifted to liposome vectors and peptide carriers, which are less problematic. Liposome vectors offer the advantage of improved directionality towards a target site due to the introduction of an antibody, protein, sugar chain or other functional molecule on the surface of the liposome.

Liposome vectors that have been developed include for example a liposome vector that incorporates a complex of a polyarginine or other coagulant and a nucleic acid in capsule form (Japanese Patent Applications Laid-open No. 2002-520038). Peptide carriers that have been developed include a membrane-permeable Tat protein derived from HIV-1, polyarginine, an arginine-rich peptide and other peptide carriers (Japanese Patent Applications Laid-open Nos. 10-33186, 2001-199997).

DISCLOSURE OF THE INVENTION

It is an object of the present invention to provide a liposome having cellular and nuclear entry ability, along with a vector for cellular and nuclear delivery of target substances using the liposome.

To solve the aforementioned problem, the present invention provides the following liposome.

(1) A liposome having on the surface thereof a peptide comprising multiple consecutive arginine residues.

(2) The liposome according to (1) above, wherein the peptide comprises 4 to 20 consecutive arginine residues.

(3) The liposome according to (1) or (2) above, wherein the peptide consists of arginine residues.

(4) The liposome according to any of (1) through (3) above, wherein the proportion of cationic lipids to total lipids making up a lipid bilayer is 0 to 40% (mole ratio).

(5) The liposome according to any of (1) through (4) above, wherein the peptide is modified with a hydrophobic group or hydrophobic compound, and wherein the hydrophobic group or hydrophobic compound is inserted into a lipid bilayer so that the peptide is exposed on the surface of the lipid bilayer.

(6) The liposome according to (5) above, wherein the hydrophobic group is a stearyl group.

(7) The liposome according to any one of (1) through (6) above, wherein is entrapped a target substance to be delivered inside a cell or nucleus.

(8) The liposome according to (7) above, wherein the target substance is a drug, nucleic acid, peptide, protein or sugar or a complex thereof.

(9) The liposome according to (8) above, wherein the target substance is a nucleic acid, and wherein a complex of the nucleic acid and a polycationic substance is entrapped.

(10) The liposome according to (9) above, wherein the polycationic substance is stearylated polyarginine.

(11) The liposome according to any of (7) through (10), which is a vector for delivery of the target substance into cells.

(12) The liposome according to any of (7) through (10), which is a vector for delivery of the target substance into nuclei.

The liposome of the present invention can accomplish efficient transport into cells and nuclei.

The liposome of the present invention can also accomplish cellular and nuclear entry at a broad range of temperatures, from 0 to 40° C. (effective temperature range is 4 to 37° C.).

Moreover, because the cellular entry route of the liposome of the present invention is not dependent wholly on endocytosis, there is no need to include a cationic lipid in the lipid bilayer, and cytotoxicity from cationic lipids can thus be minimized.

Moreover, the liposome of the present invention can achieve the same level of gene expression achieved with adenovirus vectors without the cell toxicity seen with adenovirus vectors.

Moreover, the liposome of the present invention is capable of transport into cells by means of macropinocytosis if the peptide level on its surface is adjusted. In macropinocytosis, an extracellular substance is incorporated into a cell as a fraction called a macropinosome, which unlike an endosome does not fuse with a lysosome, so that the contents of the macropinosome are not broken down by the lysosome. Hence, when the liposome of the present invention is transported into cells by means of macropiocytosis, the target substance entrapped in the liposome can be transported into cells or nuclei efficiently.

Moreover, the cellular entry route of the liposome of the present invention can be controlled by controlling the amount of peptide on the surface of the liposome of the present invention.

BEST MODE FOR CARRYING OUT THE INVENTION

Figure 1:
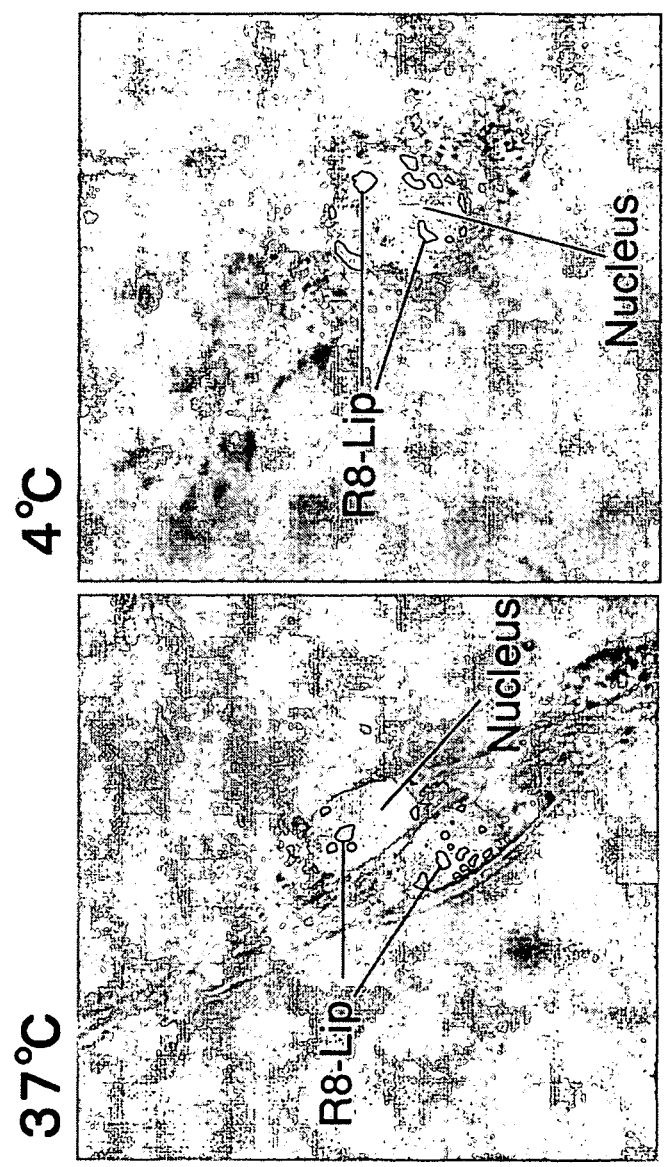
FIG. 1 shows the result of observation under a confocal laser microscope of cells incubated together with a fluorescent-labeled liposome.

The present invention is explained in detail below.

As long as the liposome of the present invention is a closed vesicle with a lipid bilayer membrane structure, there are no particular limits on the number of lipid bilayers. It may be either a multilamella vesicle (MLV) or unilamella vesicle such as an SUV (small unilamella vesicle), LUV (large unilamella vesicle), GUV (giant unilamella vesicle) or the like. There are no particular limits on the size of the liposome of the present invention, but the diameter is preferably 50 to 800 nm or more preferably 80 to 150 nm.

In the liposome of the present invention, there are no particular limits on the type of lipids making up the lipid bilayer, and specific examples include phosphatidylcholine (such as dioleoyl phosphatidylcholine, dilauroyl phosphatidylcholine, dimyristoyl phosphatidylcholine, dipalmitoyl phosphatidylcholine, distearoyl phosphatidylcholine and the like), phosphatidylglycerol (such as dioleoyl phosphatidylglycerol, dilauroyl phosphatidylglycerol, dimyristoyl phosphatidylglycerol, dipalmitoyl phosphatidylglycerol and distearoyl phosphatidylglycerol), phosphatidylethanolamine (such as dioleoyl phosphatidylethanolamine, dilauroyl phosphatidylethanolamine, dimyristoyl phosphatidylethanolamine, dipalmitoyl phosphatidylethanolamine and distearoyl phosphatidylethanolamine), phosphatidylserine, phosphatidylinositol, phosphatidic acid, cardiolipin and other phospholipids and hydrogenates thereof; and sphingomyelin, ganglioside and other glycolipids, and one or two or more of these can be used. Phospholipids may be natural lipids derived from egg yolks, soy beans or other animals or plants (such as yolk lecithin, soy lecithin and the like) or synthetic or semi-synthetic lipids.

One or two or more of the animal-derived sterols such as cholesterol, cholesterol succinic acid, lanosterol, dihydrolanosterol, desmosterol, dihydrocholesterol and the like; the plant-derived sterols (phytosterols) such as stigmasterol, sitosterol, campesterol, brassicasterol and the like; the microbiological sterols such a zymosterol, ergosterol and the like; the sugars such as glycerol, sucrose and the like; and the glycerin fatty acid esters such as triolein, trioctanoin and the like can be included in the lipid bilayer to physically or chemically stabilize the lipid bilayer or adjust the fluidity of the membrane. The content thereof is not particularly limited but is preferably 5 to 40% (mole ratio), or more preferably 10 to 30% (mole ratio) of the total lipids making up the lipid bilayer.

An antioxidant such a tocopherol, propyl gallate, ascorbyl palmitate, butylated hydroxytoluene or the like; a charged substance such as stearylamine, oleylamine or the like which contributes a positive charge; a charged substance such as dicetyl phosphate or the like which contributes a negative charge; or a membrane protein such as a peripheral membrane protein, integral membrane protein or the like can be included in the lipid bilayer, and the content thereof can be adjusted appropriately.

The liposome of the present invention has on its surface a peptide comprising multiple consecutive arginine residues. In the case of a single-membrane liposome, the outer surface of the lipid bilayer is the surface of the liposome, while in the case of a multi-membrane liposome, the surface of the liposome is the outer surface of the outermost lipid bilayer. The liposome of the present invention may also have the aforementioned peptide in a part other than the surface (such as the inner surface of a lipid bilayer).

There are no particular limits on the number of consecutive arginine residues in the aforementioned peptide as long as there is more than one, but normally there are 4-20 or preferably 6-12 or more preferably 7-10. There are no particular limits on the number of amino acid residues making up the aforementioned peptide as a whole, but normally there are 4-35 or preferably 6-30 or more preferably 8-23. The aforementioned peptide may comprise any amino acid sequence at the C-terminal and/or N-terminal of the multiple consecutive arginine residues, but preferably it consists only of arginine residues.

The amino acid sequence to be added to the C-terminal or N-terminal of the multiple consecutive arginine residues is preferably an amino acid sequence (such as polyproline) having rigidity (inflexibility). Unlike polyethylene glycol (PEG), which is soft and assumes an irregular shape, polyproline is straight and maintains a certain hardness. Moreover, the amino acid residues included in this amino acid sequence are preferably not acidic amino acids. This is because acidic amino acids, which carry a negative charge, interact statically with arginine residues, which carry a positive charge, potentially weakening the effect of the arginine residues.

The amount of the aforementioned peptide on the surface of the liposome of the present invention is normally 0.1 to 30% (mole ratio) or preferably 1 to 25% (mole ratio) or more preferably 2 to 20% (mole ratio) of the total lipids making up the lipid bilayer. If the amount of the aforementioned peptide on the surface of the liposome of the present invention is less than 2% (mole ratio) or preferably less than 1.5% (mole ratio) or more preferably less than 1% (mole ratio) of the total lipids making up the lipid bilayer, the liposome of the present invention can move into a cell or nucleus primary by means of endocytosis. The lower limit on the amount of the aforementioned peptide in this case is normally 0.1% (mole ratio) or preferably 0.5% (mole ratio) or more preferably 0.7% (mole ratio) of the total lipids making up the lipid bilayer. If the amount of the aforementioned peptide on the surface of the liposome of the present invention is 2% or more (mole ratio) or preferably 3% or more (mole ratio) or more preferably 4% or more (mole ratio) of the total lipids making up the lipid bilayer, the liposome of the present invention can move into a cell or nucleus mainly via micropinocytosis. The upper limit of the amount of the aforementioned peptide is normally 30% (mole ratio) or preferably 25% (mole ratio) or more preferably 20% (mole ratio) of the total lipids making up the lipid bilayer. In macropinocytosis, an extracellular substance is incorporated into a cell as a fraction called a macropinosome, which unlike an endosome does not fuse with a lysosome, thus preventing the contents of the macropinosome from being broken down by the lysosome. Consequently, if the liposome of the present invention moves into a cell by macropinocytosis, a target substance entrapped in the liposome of the present invention can be efficiently delivered inside the cell or nucleus.

The liposome of the present invention can move into a cell or nucleus via the aforementioned peptide on its surface. When the cellular route of a liposome is dependent on endocytosis, a cationic lipid needs to be included as a principal component of the lipid bilayer, but since the cellular entry route of the liposome of the present invention is not dependent only on endocytosis, there is no need to include a cationic lipid in the lipid bilayer. That is, the lipid bilayer of the liposome of the present invention may be composed of either a cationic lipid or a non-cationic lipid, or of both. However, since cationic lipids have cytotoxicity, the amount of cationic lipids in the lipid bilayer is preferably minimized as much as possible in order to reduce the cytotoxicity of the liposome of the present invention, and the proportion of cationic lipids relative to total lipids making up the lipid bilayer is preferably 0 to 40% (mole ratio) or more preferably 0 to 20% (mole ratio).

Examples of cationic lipids include DODAC (dioctadecyldimethylammoium chloride), DOTMA (N-(2,3-dioleyloxy)propyl-N,N,N-trimethylammonium), DDAB (didodecylammonium bromide), DOTAP (1,2-dioleoyloxy-3-trimethylammonio propane), DC-Chol (3β-N—(N',N',-dimethyl-aminoethane)-carbamol cholesterol), DMRIE (1,2-dimyristoyloxypropyl-3-dimethylhydroxyethyl ammonium), DOSPA (2,3-dioleyloxy-N-[2(sperminecarboxamido)ethyl]-N,N-dimethyl-1-propanaminum trifluoroacetate) and the like.

A "non-cationic lipid" is a neutral lipid or anionic lipid, and examples of neutral lipids include for example diacylphosphatidylcholine, diacylphosphatidylethanolamine, cholesterol, ceramide, sphingomyelin, cephalin, cerebroside and the like, while examples of anionic lipids include for example cardiolipin, diacylphosphatidylserine, diacylphosphatidic acid, N-succinyl phosphatidylethanolamine (N-succinyl PE), phosphatidic acid, phosphatidylinositol, phosphatidylglycerol, phosphatidylethylene glycol, cholesterol succinic acid and the like.

An example of a preferred mode of the liposome of the present invention is a liposome in which the aforementioned peptide is modified with a hydrophobic group or hydrophobic compound, and the hydrophobic group or hydrophobic compound is inserted into the lipid bilayer so that the aforementioned peptide is exposed on the surface of the lipid bilayer. In this mode, "exposed on the surface of the lipid bilayer" includes cases in which the peptide is exposed on either the outer or inner surface of the lipid bilayer, or on both surfaces.

There are no particular limits on the hydrophobic group or hydrophobic compound as long as it is inserted into the lipid bilayer. Examples of hydrophobic group include for example stearyl and other saturated and unsaturated fatty acid groups, cholesterol groups and derivatives thereof, but of these a fatty acid group with 10 to 20 carbon atoms (such as a palmitoyl, oleoyl, stearyl or arachidoyl group or the like) is preferred. Examples of hydrophobic compounds include for example the aforementioned phospholipids, glycolipids and sterols, long-chain aliphatic alcohols (such as phosphatidylethanolamine, cholesterol, etc.), polyoxypropylene alkyls, glycerin fatty acid esters and the like.

The liposome of the present invention can be prepared for example by a known method such as hydration, ultrasonic treatment, ethanol injection, ether injection, reverse-phase evaporation, the surfactant method, freezing and thawing or the like.

The manufacture of a liposome by hydration is described below.

A lipid which is a component of the lipid bilayer is dissolved in an organic solvent together with the aforementioned peptide modified with a hydrophobic group or hydrophobic compound, and the organic solvent is removed by evaporation to obtain a lipid membrane. The organic solvent used here may be for example a hydrocarbon such as pentane, hexane, heptane, cyclohexane or the like; a halogenated hydrocarbon such as methylene chloride, chloroform or the like; an aromatic hydrocarbon such as benzene, toluene or the like; a lower alcohol such as methanol, ethanol or the like; an ester such as methyl acetate, ethyl acetate or the like; or a ketone such as acetone or the like, and one or a combination of two or more of these can be used. Next, the lipid membrane is hydrated, and agitated or ultrasound treated to manufacture a liposome having the aforementioned peptide on its surface.

Another manufacturing example using hydration is described below.

A lipid which is a component of the lipid bilayer is dissolved in an organic solvent, and the organic solvent is then removed by evaporation to obtain a lipid membrane which is hydrated and agitated or ultrasound treated to manufacture a liposome. Next, the aforementioned peptide modified with a hydrophobic group or hydrophobic compound is added to the external solution of the liposome to introduce the aforementioned peptide into the surface of the liposome.

Liposomes having a fixed particle distribution can be obtained by passing the liposomes through a filter of a specific pore size. A multi-membrane liposome can also be converted to a single-membrane liposome or a single-membrane liposome can be converted to a multi-membrane liposome by known methods.

A target substance to be delivered inside a cell or nucleus can be entrapped within the liposome of the present invention.

There are no particular limits on the type of target substance, and examples include drugs, nucleic acids, peptides, proteins, sugars and complexes of these and the like which can be selected appropriately according to the objective of diagnosis, treatment or the like. "Nucleic acids" include not only DNA or RNA but also analogs or derivates of these (such as peptide nucleic acids (PNAs), phosphorothioate DNA and the like). The nucleic acid may be single-stranded or double-stranded, and may be either linear or cyclic.

When the target substance is water-soluble, the target substance can be included in the water phase inside the liposome by adding the target substance to the aqueous solvent used for hydrating the lipid film during liposome manufacture. If the target substance is liposoluble, the target substance can be included in the lipid bilayer of the liposome by adding the target substance to the organic solvent used for liposome manufacture.

When the target substance is a nucleic acid, the nucleic acid to be included is preferably made in advance into a complex with a cationic substance. A liposome containing a complex of a nucleic acid and a cationic substance can be easily and efficiently manufactured by hydrating the lipid film in the presence of the complex of a nucleic acid and a cationic substance, and then agitating or ultrasound treating it.

A "cationic substance" is a substance having a cationic group in the molecule, which is capable of forming a complex through electrostatic interaction with a nucleic acid. There are no particular limits on the type of cationic substance as long as it can form a complex with a nucleic acid, but examples include cationic lipids (such as Lipofectamine (Invitrogen)); polymers having cationic groups; polylysine, polyarginine, copolymers of lysine and arginine and other homopolymers or copolymers of basic amino acids, or derivatives of these (such as stearylated derivatives); polyethyleneimine and other polycationic polymers; and protamine sulfate and the like, but of these stearylated polyarginine is especially desirable. The number of arginine residues making up the polyarginine is normally 4 to 20 or preferably 6 to 12 or more preferably 7 to 10. There are no particular limits on the number of cationic groups in the cationic substance, but 2 or more is preferable. There are no particular limits on the cationic groups as long as they can be positively charged, and examples include amino, methylamino, ethylamino and other monoalkylamino groups; dimethylamino, diethylamino and other dialkylamino groups; and imino and guanidino groups and the like.

Since a complex of a nucleic acid and a cationic substance carries a plus charge or a minus charge overall depending on the relative proportions, the aforementioned complex can be efficiently entrapped inside the liposome by means of electrostatic interaction with non-cationic or cationic lipids.

Since a lipid membrane obtained by dissolving a lipid which is a component of the lipid bilayer in an organic solvent together with the aforementioned peptide modified with a hydrophobic group or hydrophobic compound, and then removing the organic solvent by evaporation, contains the aforementioned peptide which is a cationic substance, the electrostatic interaction between the aforementioned complex and lipid membrane may be weakened depending on the composition. In these cases, it is preferable to use a lipid membrane that does not contain the aforementioned peptide. A lipid membrane that does not contain the aforementioned peptide can be obtained by first dissolving a lipid which is a constituent of the lipid bilayer in an organic solvent without dissolving the aforementioned peptide modified with a hydrophobic group or hydrophobic compound in the organic solvent, and then removing the organic solvent by evaporation. The aforementioned peptide is then introduced onto the liposome surface after formation of the liposome with the aforementioned complex entrapped therein.

A liposome including a target substance can be used as a vector for delivery of a target substance into a cell or nucleus.

The organism used to derive the cell into which the target substance is delivered is not particularly limited, and may be an animal, plant, microorganism or the like, but an animal is preferred and a mammal is particularly preferred. Examples of mammals include humans, monkeys, cows, sheep, goats, horses, pigs, rabbits, dogs, cats, rats, mice, guinea pigs and the like. There are no particular limits on the type of cell to which the target substance is delivered, and examples include somatic cells, reproductive cells, stem cells and cultured cells of these and the like.

The liposome of the present invention can be used for example as a liquid dispersion. Dispersion solvents that can be used include physiological saline, phosphate buffer, citric buffer, acetic acid buffer and other buffers. Sugars, polyvalent alcohols, water-soluble polymers, non-ionic surfactants, antioxidants, pH adjusters, hydration promoters and other additives can also be added to the dispersion.

The liposome of the present invention can be used as a dried (such as freeze-dried, spray-dried or the like) dispersion. The dried liposome can then be made into a liquid dispersion through addition of a buffer such as physiological saline, phosphate buffer, citric buffer, acetic acid buffer or the like.

The liposome of the present invention can be used both in vivo and in vitro. When using the liposome of the present invention in vivo, it can be administered by a parenteral route such as intravenously, intraperitoneally, subcutaneously, nasally or the like for example, and the dose and number of administrations can be adjusted appropriately according to the type and amount of target substance entrapped in the liposome and the like. Since the liposome of the present invention exhibits cellular and nuclear entry ability at a broad range of temperatures from 0 to 40° C. (with an effective temperature range of 4 to 37° C.), the temperature conditions can be set according to the objective. To effectively accomplish cellular and nuclear entry at low temperatures (normally 4 to 10° C. or preferably 4 to 6° C.), the liposome of the present invention needs to move into a cell or nucleus without endocytosis. If the amount of the aforementioned peptide on the surface of the liposome of the present invention is 2% or more (mole ratio) or preferably 3% or more (mole ratio) or more preferably 4% or more (mole ratio) of the total lipids making up the lipid bilayer, the liposome of the present invention can effectively achieve cellular and nuclear entry at low temperatures (normally 4 to 10° C. or preferably 4 to 6° C.). The upper limit of the amount of the aforementioned peptide in this case is normally 30% (mole ratio) or preferably 25% (mole ratio) or more preferably 20% (mole ratio) of the total lipids making up the lipid bilayer.

EXAMPLES

Example 1

Preparation of Liposome with Cellular and Nuclear Entry Ability

A liposome having octaarginine on its surface was prepared by hydration as follows. 0.75 mg of stearylated octaarginine was dissolved in 9.0 mL of ethanol, while 5.02 mg of egg yolk phosphatidylcholine and 1.1 mg of cholesterol were dissolved in 21 mL of chloroform. The two solutions were mixed, and placed in a round-bottomed flask (final chloroform:ethanol ratio=7:3). The solvent was removed with a rotating evaporator, and the remainder was dried for 2 hours in a desiccator. The resulting lipid membrane (10 μmole) was hydrated in 1 mL of phosphate-buffered saline which had been warmed in advance to 50° C., and agitated for 5 seconds. The lipid dispersion was passed 11 times each through 400 nm, 200 nm and 100 nm polycarbonate membrane filters. In this way, a liposome was formed having octaarginine (5 mole % of total lipids) on its surface.

The liposome was fluorescent labeled by incorporating 1% rhodamine (Rho) or 1% rhodamine-labeled phosphatidylethanolamine (Rho-PE) (red). The water phase marker Rho was dissolved in the solvent for hydration, while the lipid phase marker Rho-PE was dissolved in the chloroform solution.

NIH3T3 cells ($2.5 \times 10^5$ cells/60 mm dish) were incubated overnight in DMEM containing 10% FBS under confocal laser microscopic observation. Next, the NIH3T3 cells were incubated in serum-free DMEM medium liquid containing the fluorescent-labeled liposome (final lipid concentration 0.1 μM). Incubation was for 1 or 3 hours at 37° C. or 4° C. When the temperature was 4° C., the cells were preincubated for 30 minutes at 4° C., and maintained at that temperature until observation. After incubation was complete the cells were washed and then observed by confocal laser microscopy without being fixed. The cell nuclei were stained using the fluorescent dye SYTO24 (green).

The results of observation by confocal laser microscopy are shown in FIG. 1. In FIG. 1, the left side show the results at 37° C. and the right side the results at 4° C. "R8-Lip" indicates the location of a liposome having octaarginine on its surface (small white part circled with black line), while "Nucleus" indicates the position of a nucleus (large white part).

As shown in FIG. 1, liposomes were observed in the cytoplasm and nuclei of almost all cells at both temperatures. Using conventional transfection agents such as LipofectAMINE (Invitrogen), only about 30 to 50% of the total cells are transfected. Intercellular fluorescence detected after incubation at 4° C. was about 70% of intercellular fluorescence detected after incubation at 37° C.

These results show that a liposome having octaarginine on its surface has cellular and nuclear entry ability, being able to move into cells or nuclei not only at 37° C. but also at a low temperature of 4° C.

Example 2

Gene Delivery into Cells Using the Liposome

8 μg of a plasmid with a total length of 8454 bp comprising the luciferase gene and a CMV promoter upstream therefrom (this plasmid was prepared by incorporating luciferase gene into PQBI plasmid having CMV promoter) and 16 µg of stearylated arginine were mixed by agitation in 10 mM HEPES buffer to prepare a complex of the aforementioned plasmid and stearylated arginine.

125 µL of a solution obtained by dissolving 0.672 mg of dioleoylphosphatidylethanolamine and 0.096 mg of cholesterol succinic acid in 1 mL of chloroform was taken in a glass test tube, and nitrogen gas was blown thereon to evaporate it to dryness, forming a lipid membrane.

250 µL liquid containing the aforementioned complex was added to the lipid membrane, and left 10 minutes at room temperature to hydrate the membrane. After hydration this was ultrasound treated for a few seconds in an ultrasound tank to prepare a liposome with the aforementioned complex entrapped therein. 12 µL of 1 mg/mL stearylated octaarginine solution was added to the external liquid of the liposome, and left for 30 minutes at room temperature to introduce octaarginine (5 mole % of total lipids) into the surface of the liposome.

(i) 12.5 µL (equivalent to 0.4 µg DNA) of the aforementioned plasmid-stearylated arginine complex, (ii) 12.5 µL (equivalent to 0.4 µg DNA) of the liposome having the aforementioned complex entrapped therein and octaarginine on the surface, or (iii) 4 µL of LipofectAMINE PLUS reagent (Invitrogen), currently the strongest-known gene-introduction reagent, the aforementioned plasmid (equivalent to 0.4 µg DNA) and 1 µL of LipofectAMINE were added to $4 \times 10^4$ NIH3T3 cells, and cultured for 3 hours at 37° C. without serum. They were then cultured for 45 hours at 37° C. with serum, and luciferase expression activity (RLU/mg protein) was compared. Luciferase expression activity was measured by adding luciferase activity measurement reagent (luciferase assay system, Promega) to the cell lysate and measuring chemoluminescence with a luminometer.

Figure 2:
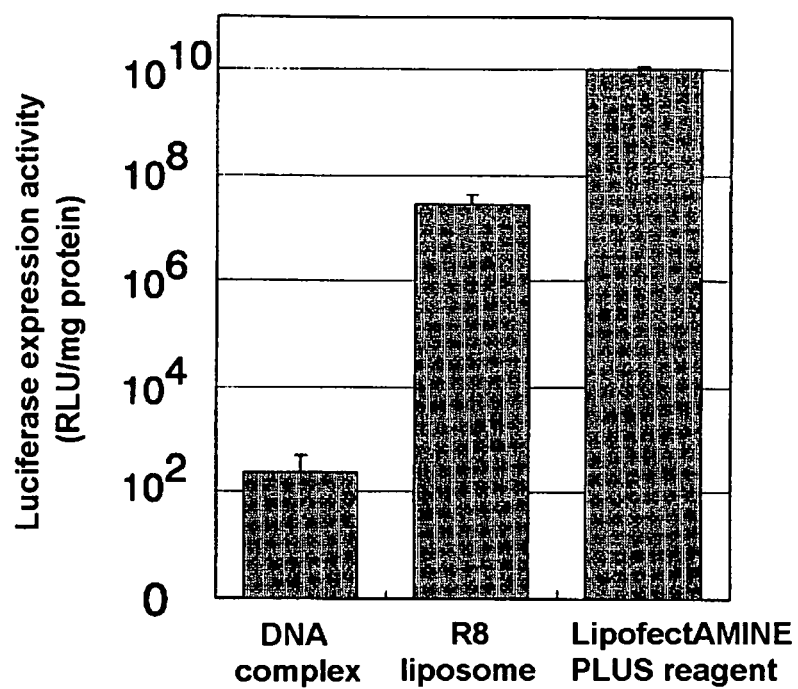
FIG. 2 shows the results of measurement of luciferase expression activity under various conditions.

Measurement results for luciferase expression activity are shown in FIG. 2. In FIG. 2, "DNA complex" corresponds to (i) above, "R8 liposome" to (ii) above and "LipofectAMINE PLUS reagent" to (iii) above.

As shown in FIG. 2, luciferase expression activity was lowest with the complex of the aforementioned plasmid and stearylated arginine because it was affected by degradation enzymes in the serum and the like. The highest luciferase expression activity was seen with the LipofectAMINE PLUS reagent (about $1 \times 10^{10}$ RLU/mg protein), but cytotoxicity occurred. In the case of the liposome containing the aforementioned complex and having octaarginine introduced on the surface, activity was close to that obtained with LipofectAMINE PLUS (about $1 \times 10^8$ RLU/mg protein), and there was no cytotoxicity. Cell toxicity is investigated in more detail in Example 3.

These results show that efficient gene delivery into a cell or nucleus can be achieved if the gene is entrapped in a liposome with octaarginine introduced on its surface.

Example 3

Evaluation of Liposome Cytotoxicity

Cytotoxicity was compared and studied for (i), (ii) and (iii) in Example 2 by a cell survival assay (MTT assay) using formazan dye production by mitochondria in living cells.

Specifically, cell survival (%) was measured by MTT assay following 48 hours of thermostatic treatment at 37° C. under the same conditions as in Example 2—that is, with $4 \times 10^4$ NIH3T3 cells exposed to reagent equivalent to 0.4 µg DNA.

As a control, cell survival (%) was measured in the same way when treatment was with the aforementioned plasmid alone.

Figure 3:
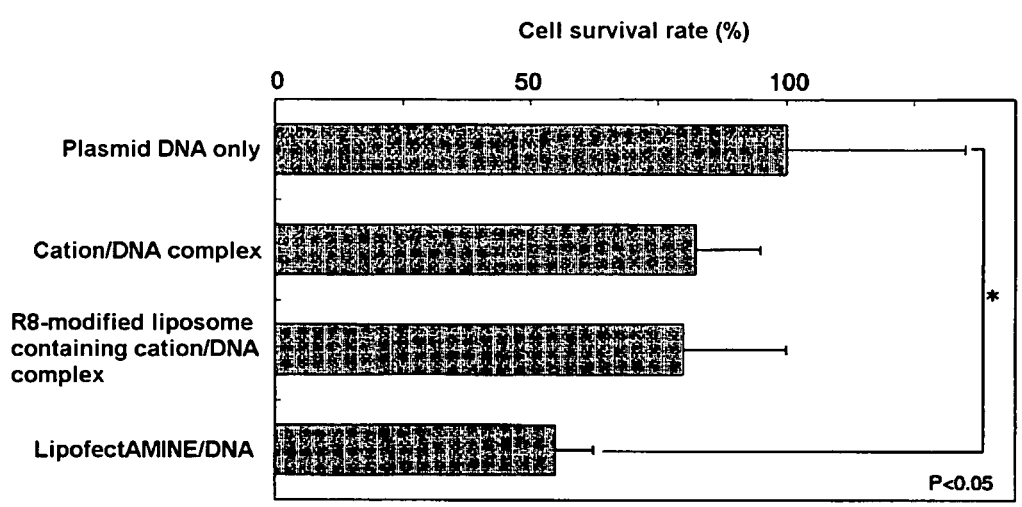
FIG. 3 shows the results of measurement of cell survival (%) under various conditions.

The measurement results for cell survival (%) are shown in FIG. 3. As shown in FIG. 3, cell survival declined slightly in the case of the complex of the aforementioned plasmid with stearylated arginine (Example 2(i), "cation/DNA complex" in FIG. 3) and the liposome having the aforementioned complex entrapped therein and octaarginine introduced on the surface (Example 2(ii), "R8-modified liposome containing cation/DNA complex" in FIG. 3), but not significantly. However, the survival rate of the cells treated with the LipofectAMINE PLUS reagent (Example 2(iii), "LipofectAMINE/DNA" in FIG. 3) declined significantly, by about 50%.

The results show that a liposome having octaarginine introduced on the surface has low cytotoxicity.

Example 4

Investigation of Cellular Entry Route of Liposome

NIH3T3 cells were incubated in the presence (final lipid concentration 0.1 mM) of a liposome having octaarginine introduced on the surface (stearylated octaarginine content 5 mole % of total lipids). The cells were incubated for 1 hour at 37° C. or 4° C. in the presence of sucrose (0.3 M, hypertonic solution), an endocytosis inhibitor mixture (1 µg/mL antimycin A, 10 mM NaF and 0.1% sodium azide), or nystatin (25 µg/mL). The NIH3T3 cells were pre-incubated for 30 minutes in the presence of the endocytosis inhibitor mixture before addition of the liposome. When incubation was complete the solvent was removed, and the NIH3T3 cells were washed thrice and observed under a confocal laser microscope.

Figure 4:
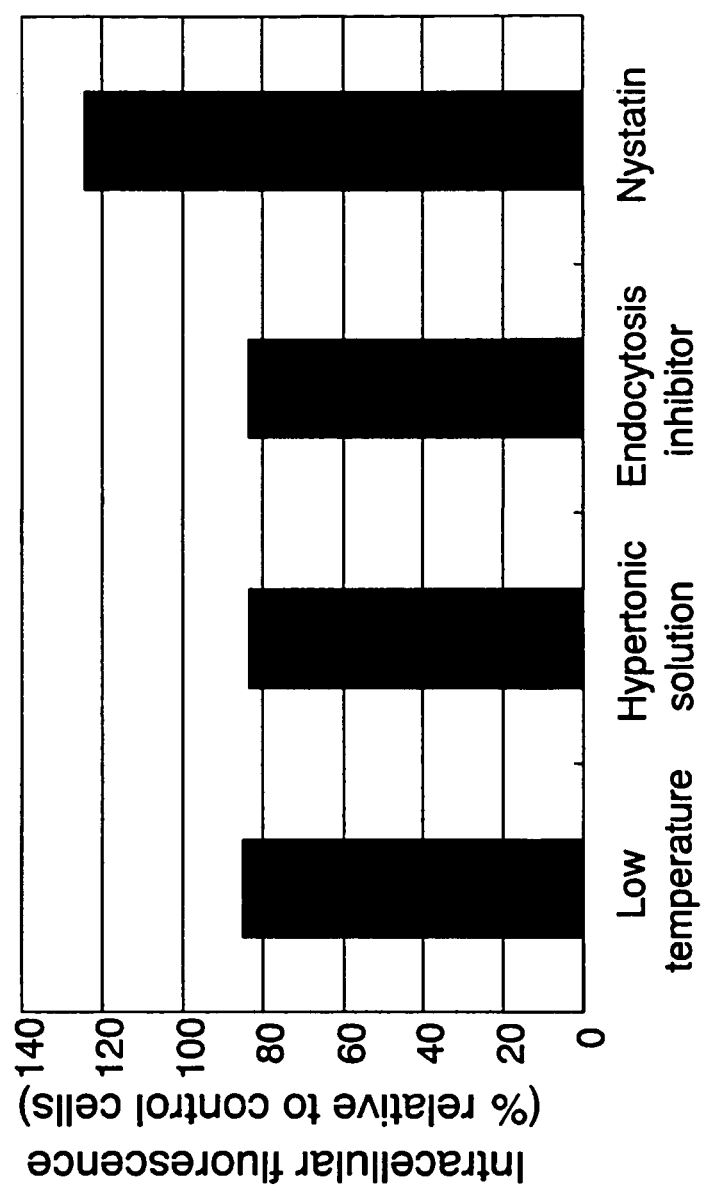
FIG. 4 shows the results of a comparison of the areas of intracellular regions in which fluorescence was observed under various conditions.

In each case, the area of the intercellular regions where fluorescence was observed was totaled and averaged for at least 15 cells, and calculated as a proportion of the mean value for the control cells. The results are shown in FIG. 4. In FIG. 4, "low temperature" indicates the results at 4° C., while "hypertonic solution", "endocytosis inhibitor" and "nystatin" indicate the results at 37° C.

As shown in FIG. 4, treatment with the endocytosis inhibitor produced no significant decline in the area of the intercellular regions where fluorescence was observed. This shows that the route by which a liposome with octaarginine introduced on the surface moves into cells is not dependent solely on endocytosis.

Example 5

Comparison with Adenovirus Vector

As in Example 2, a liposome was prepared having a complex of stearylated arginine with a plasmid having the luciferase gene and a CMV promoter upstream therefrom entrapped therein and having octaarginine introduced on the surface ("R8 liposome" in FIG. 5), and this liposome (equivalent to 0.4 µg DNA) suspended in 0.25 mL serum-free DMEM medium was added to HeLa cells or A549 cells cultured on 24-well plates ($4 \times 10^4$ cells/well each) and incubated for 3 hours at 37° C. After 3 hours, 1 mL of medium containing 10% fetal bovine serum was added and incubated for a further 45 hours. The cells were then lysed, a luciferase activity measurement reagent (luciferase assay system, Promega) was added to the cell lysate, and luciferase activity was measured with a luminometer (Luminescencer PSN, Atto). The amount of protein in the cell lysate was measured using a BCA protein assay kit (PIERCE, Rockford, Ill.). As a control, luciferase activity and protein level were also measured as above using the aforementioned complex plasmid-stearylated arginine complex not entrapped in a liposome (equivalent to 0.4 μg DNA) ("DNA complex" in FIG. 5).

An adenovirus was prepared with the luciferase gene incorporated therein (Type 5 adenovirus lacking E1-, E3- and replication ability and comprising a cytomegalovirus promoter/enhancer and luciferase gene at the E1 gene position). This adenovirus was amplified using HEK293 human embryonic kidney cells, and purified by cesium chloride gradient centrifugation. An adenovirus suspension ($5 \times 10^3$ particles/cell or $1 \times 10^5$ particles/cell) was added to HeLa cells or A549 cells cultured on 24-well plates ($4 \times 10^4$ cells/well each), and incubated for 3 hours at 37° C. in 0.25 mL of medium containing no serum. Next, 1 mL of 10% fetal bovine serum medium was added and incubated for 45 hours. After incubation, luciferase activity and protein level were measured as above.

Figure 5:
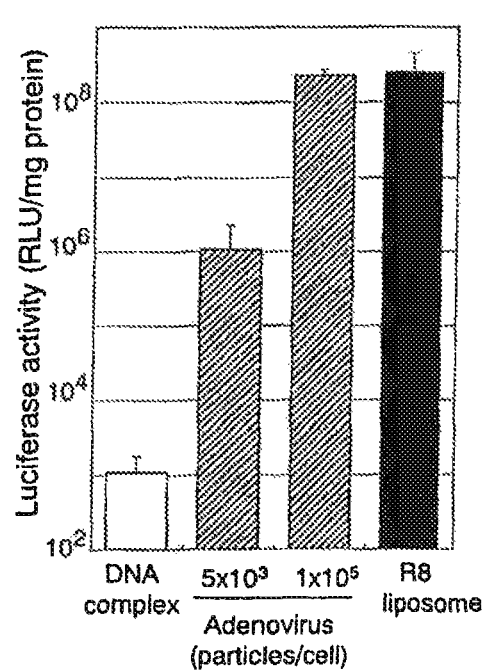
FIG. 5 shows the results of measurement of luciferase expression activity under various conditions.
Figure 5:
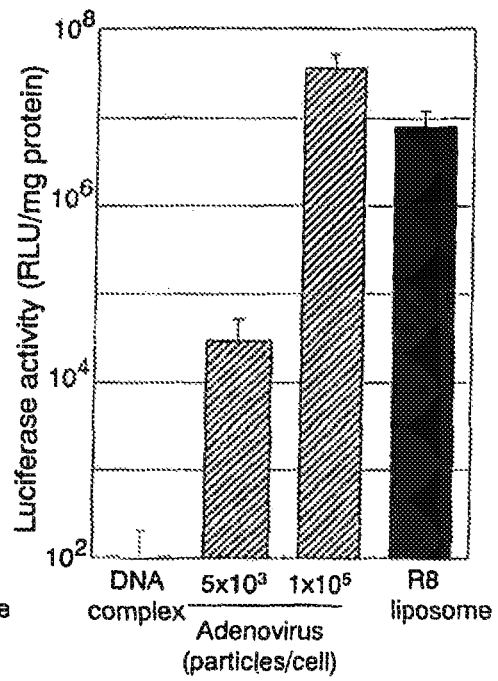

The measurement results for luciferase activity are shown in FIG. 5. FIG. 5(A) shows the results using HeLa cells, while FIG. 5(B) shows the results using A549 cells.

An adenovirus concentration of $5 \times 10^3$ particles/cells is a commonly reported concentration, while an adenovirus concentration of $1 \times 10^5$ particles/cell is a higher concentration used to obtain a higher level of luciferase activity. Because adenoviruses exhibit extremely strong cytotoxicity, the adenovirus concentration could not be raised above $1 \times 10^5$ particles/cell.

As shown in FIG. 5, the liposome having the plasmid-stearylated arginine complex entrapped therein and having octaarginine introduced on the surface produced about the same level of luciferase activity as an adenovirus concentration of $1 \times 10^5$ particles/cell, with no cytotoxicity. These results show that a liposome having octaarginine introduced on the surface produces the same level of gene expression activity as an adenovirus vector without the cell toxicity seen with adenovirus vectors.

Example 6

Investigation of Cellular Entry Route of Liposome

NIH3T3 cells were first treated for 10 minutes with the endocytosis inhibitor sucrose (0.4 M) or the macropinocytosis inhibitor Amiloride (2.5 mM), and then incubated for 1 hour after addition of a liposome having a complex of stearylated arginine and a plasmid having the luciferase gene with a CMV promoter upstream therefrom entrapped therein and octaarginine introduced on the surface (see Example 2) (equivalent to 0.4 μg DNA). The medium was then removed and the cells were washed thrice with PBS containing 20 U/mL heparin and then once with PBS. After being washed they were incubated for 70 minutes in serum-free medium, and then incubated for 12 hours after addition of 1 mL of medium containing 10% fetal bovine serum. After 12 hours of incubation, luciferase activity was measured as in Example 5. NIH3T3 cells pre-treated without the endocytosis inhibitor sucrose and the macropinocytosis inhibitor Amiloride were used as a control.

Figure 6:
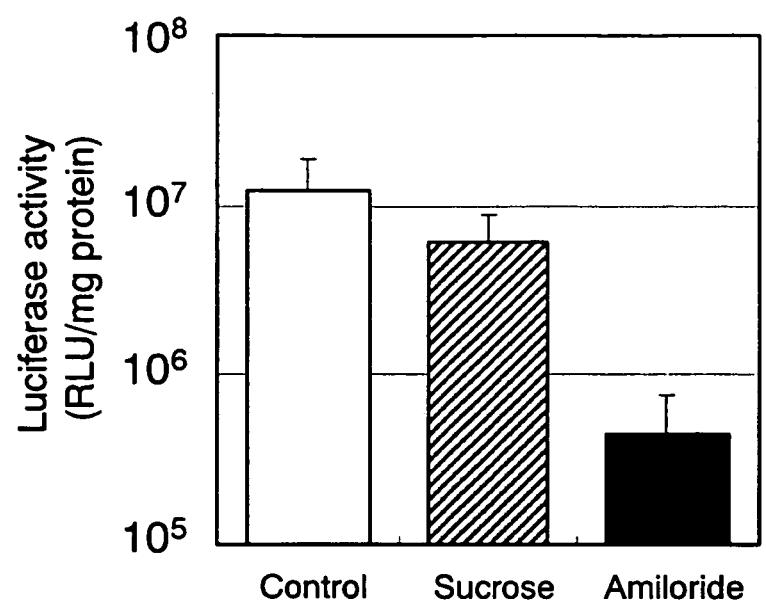
FIG. 6 shows the results of measurement of luciferase expression activity under various conditions.

The results are shown in FIG. 6.

As shown in FIG. 6, when the cells were pre-treated with the endocytosis inhibitor sucrose there was no obvious effect, but when they were pre-treated with the macropinocytosis inhibitor Amiloride luciferase activity declined dramatically.

It is thought that in macropinocytosis because the extracellular substance is incorporated into the cell in the form of a fraction called a macropinosome, which unlike an endosome does not fuse with the lysosome, the contents of the macropinosome are not broken down by the lysosome. This suggests that the route of movement into cells of a liposome having octaarginine introduced on the surface is via macropinocytosis.

Example 7

Investigation of Cellular Entry Route of Liposome

NIH3T3 cells were first incubated for 30 minutes at 37° C. in the presence of either metabolic inhibitors (comprising 0.1% sodium azide, 10 mM sodium fluoride and 1 μg/mL antimycin A) or the endocytosis inhibitor sucrose (0.4 M), or for 10 minutes at 37° C. in the presence of the macropinocytosis inhibitor Amiloride (5 mM), or for 30 minutes at 4° C. without any inhibitors, and were then incubated for 1 hour after addition of a liposome having octaarginine introduced on the surface and rhodamine dye entrapped in the inner water phase (octaarginine content 0.8 mole % or 5 mole % of total lipids). Next, the cells were washed with PBS containing 20 U/mL heparin, then trypsin treated, centrifuged, and washed twice again with PBS containing heparin. The washed cells were filtered with nylon mesh and analyzed with a flow cytometer (FACScan, Becton, Dickinson and Company). Cells incubated for 30 minutes at 37° C. without any inhibitor were used as the control, and cellular incorporation (%) was evaluated in each instance relative to 100% as the cellular incorporation value of the control.

Figure 7:
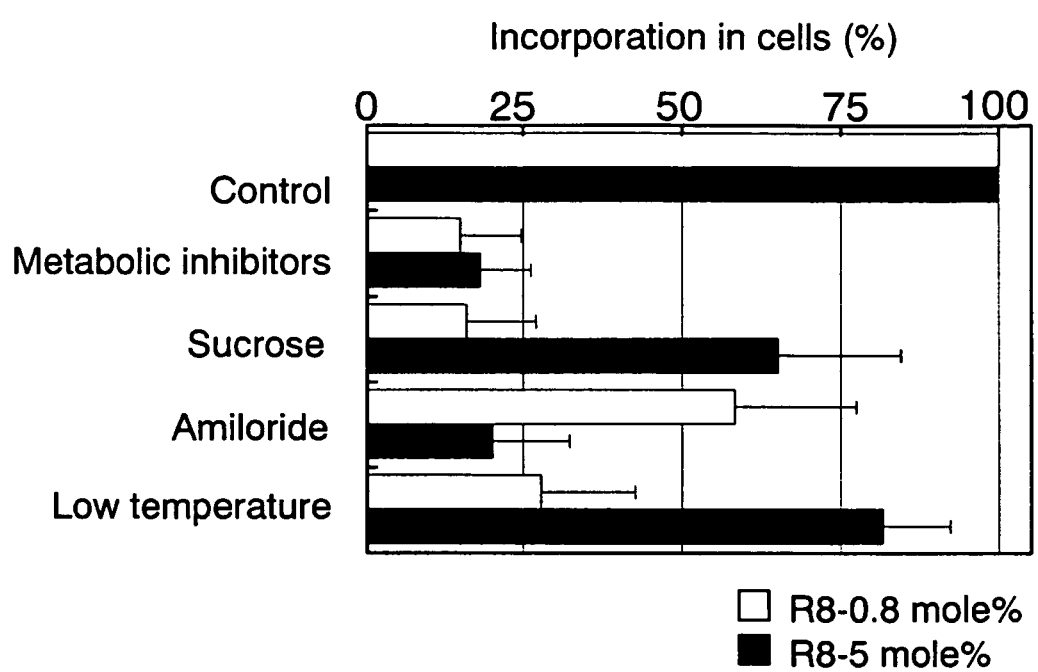
FIG. 7 shows the results of measurement of the amount of liposome incorporated into cells under various conditions.

The results are shown in FIG. 7.

As shown in FIG. 7, when the octaarginine content was 0.8% mole of total lipids, incorporation into cells was markedly inhibited by the presence of metabolic inhibitors and the endocytosis inhibitor sucrose and by low temperature (4° C.). When the octaarginine content was 5% mole of total lipids, however, incorporation into cells was markedly inhibited by the presence of metabolic inhibitors and the macropinocytosis inhibitor Amiloride.

These results suggest that (1) a liposome having octaarginine introduced on the surface is incorporated into cells by a route that requires energy regardless of the octaarginine content, (2) when the octaarginine content is 0.8% mole of total lipids, a liposome having octaarginine introduced on the surface is incorporated into cells via endocytosis, (3) when the octaarginine content is 5% mole of total lipids, a liposome having octaarginine introduced on the surface is incorporated into cells via macropinocytosis, and (4) incorporation into cells at low temperatures (4° C.) is not induced when the octaarginine content is low. That is, it has been shown that the cellular entry route of a liposome having octaarginine introduced on the surface can be controlled by controlling the octaarginine content.

The invention claimed is:

1. A liposome for delivery of a target substance into cells, the liposome having one or more lipid bilayers,
   wherein each lipid bilayer comprises an inner and outer surface,
   wherein the inner and outer surface of each lipid bilayer consists of a single type of peptide,
   wherein the peptide consists of 7 to 10 consecutive arginine residues,
   wherein the peptide is modified with a hydrophobic group selected from the group consisting of saturated or unsaturated fatty acids capable of being inserted into said lipid bilayer consisting of noncationic lipids, wherein the hydrophobic group is inserted into each lipid bilayer so that the peptide is exposed on the inner and outer surface of the lipid bilayer, and wherein the amount of the modified peptide is 2% or more (molar ratio) of the total lipids making up each lipid bilayer.

2. The liposome according to claim 1, wherein the peptide consists of 8 consecutive arginine residues.

3. The liposome according to claim 1, wherein the hydrophobic group is a stearyl group.

4. The liposome according to claim 1, wherein is entrapped a target substance to be delivered inside a cell or nucleus.

5. The liposome according to claim 4, wherein the target substance is a drug, nucleic acid, peptide, protein or sugar or a complex thereof.

6. The liposome according to claim 5, wherein the target substance is a nucleic acid molecule, and wherein a complex of the nucleic acid molecule and a polycationic substance it entrapped.

7. The liposome according to claim 5, wherein the polycationic substance is stearylated polyarginine.

8. The liposome according to any of claims 4 through 7, which is a vector for delivery of the target substance into cells.

9. The liposome according to any of claims 4 through 7, which is a vector for delivery of the target substance into nuclei.

10. A liposome for delivery of a target substance into cells, the target substance being entrapped within the liposome and being a complex of a nucleic acid molecule and stearylated polyarginine, the liposome further having one or more lipid bilayers, wherein each lipid bilayer comprises an inner and outer surface, wherein the inner and outer surface of each lipid bilayer consists of a single type of peptide, wherein the peptide consists of 7 to 10 consecutive arginine residues, wherein the peptide is modified with a hydrophobic group selected from the group consisting of saturated or unsaturated fatty acids capable of being inserted into said lipid bilayer consisting of noncationic lipids, wherein the hydrophobic group is inserted into each lipid bilayer so that the peptide is exposed on the inner and outer surface of the lipid bilayer, and wherein the amount of the modified peptide is 2% or more (molar ratio) of the total lipids making up each lipid bilayer.

11. The liposome of claim 1 wherein the amount of the modified peptide is no greater than 30% (molar ratio) of the total lipids making up the lipid bilayer.

12. A modified liposome for delivery of a target substance into cells by macropinocytosis consisting of:

a liposome having one or more lipid bilayers, wherein each lipid bilayer comprises an inner and outer surface, wherein the inner and outer surface of each lipid bilayer consists of a single type of peptide, wherein the peptide consists of 7 to 10 consecutive arginine residues, wherein the peptide is modified with a hydrophobic group selected from the group consisting of saturated or unsaturated fatty acids capable of being inserted into said lipid bilayer consisting of noncationic lipids, wherein the hydrophobic group is inserted into each lipid bilayer so that the peptide is exposed on the inner and outer surface of the lipid bilayer, and wherein the amount of the modified peptide is 2% or more (molar ratio) of the total lipids making up each lipid bilayer.

13. The liposome of claim 12 wherein the amount of the modified peptide is no greater than 30% (molar ratio) of the total lipids making up the lipid bilayer.

\* \* \* \* \*